United States Patent [19]

Snow et al.

[11] Patent Number: 4,992,269

[45] Date of Patent: Feb. 12, 1991

[54] ANIMAL REPELLANT

[75] Inventors: Roger Snow, Sandringham; Philip B. Alldritt, Bundoora, both of Australia

[73] Assignee: Hot Foot International Pty. Ltd., Melbourne, Australia

[21] Appl. No.: 885,812

[22] Filed: Jul. 15, 1986

Related U.S. Application Data

[63] Continuation of Ser. No. 620,944, Jun. 15, 1984, abandoned.

[30] Foreign Application Priority Data

Sep. 15, 1983 [AU] Australia .............................. 1431/83

[51] Int. Cl.$^5$ ............................................. A01N 25/00
[52] U.S. Cl. ...................................... 424/83; 424/84; 514/918
[58] Field of Search ............................. 424/80, 81, 83; 514/918

[56] References Cited

U.S. PATENT DOCUMENTS 3,378,439  4/1968  Reinert et al. ..................... 514/918

FOREIGN PATENT DOCUMENTS 487582  3/1970  Switzerland .

OTHER PUBLICATIONS

Gelants for Organic and Water-Based Systems. Tixogel VP, Tixogel VZ and Tixogel WM, United Catalysts, Inc., Louisville, Ky., (1981).
Hyvis Polybutenes, BP Chemicals Ltd., (1980).

Primary Examiner—Douglas W. Robinson
Attorney, Agent, or Firm—Merchant, Gould, Smith, Edell, Welter & Schmidt

[57] ABSTRACT

A bird repellant composition including
 an effective amount of a polymeric component which polymeric component includes at least one butene polymer or copolymer, and
 an effective amount of a thickening agent.

9 Claims, No Drawings

# ANIMAL REPELLANT

This is a continuation of application Ser. No. 620,944, filed June 15, 1984, now abandoned.

The present invention relates to animal repellants, particularly bird repellants. Bird repellants are well known. In general, bird repellant compositions function by coating at least a part of the surface to be protected with a tacky composition, contact with which will repel the birds. However, known bird repellant compositions are deficient in a number of aspects. In particular, whilst the composition should be sticky or tacky, if it is too tacky it will pick up dust, leaves, etc. quickly and be rendered inefficient very quickly. Moreover, birds may become stuck to this surface. Similarly, the composition must be such that it is weather resistant and in such a form which will minimize flattening. It would be particularly advantageous if a bird repellant composition could be provided in a gel or bead form for delivery in cartridges such as is used for adhesives etc.

It is particularly advantageous to have a composition which may be delivered in a cartridge or like form since (apart from the obvious convenience), the delivery of the composition in the form of a bead allows for the coverage of a greater area effectively with the same amount of material. Moreover, drying out of the composition which will lead to deterioration thereof is minimized. The flattening of the composition is also, minimized. It is a further advantage if the composition does not stain or damage any painted or preferred surface.

A further deficiency of bird repellant compositions of the prior art has been that they are ineffective in relation to certain types of birds. In particular, it has been noted that certain compositions are ineffective against certain birds but are effective against others. Particular difficulties are encountered with pigeons, starlings and seagulls. It would be an advantage to have a bird repellant composition which would be effective against these types of birds in particular, as well as others.

Accordingly, it is an object of the present invention to overcome or at least alleviate at least some of the difficulties and deficiencies of the prior art.

Accordingly, in one aspect of the present invention there is provided a bird repellant composition which includes
  (a) an effective amount of a polymeric component which polymeric component includes at least one butene polymer or copolymer, and
  (b) an effective amount of a thickening agent.

It has been found that the bird repellant composition according to the first aspect of the present invention is effective against numerous types of birds including starlings, pigeons and large web-footed birds including seagulls and the like.

The polymeric component (a) may be present in an amount sufficient to provide a bird repellant composition with a desired degree of tackiness. The bird repellant composition should preferably be of sufficient tackiness to repel birds but not so tacky as to substantially retard the birds.

The polymeric component (a) may be present in a major amount of the composition. The polymeric component may be present in amounts of from approximately 75 to 98% by weight of the bird repellant composition. The polymeric component may be present in amounts of from approximately 92.5% to 97.5% by weight of total composition, preferably 93% by weight.

The polymeric component may include at least one butene polymer. The at least one butene polymer may comprise a major amount of the polymeric composition. In a preferred form the at least one butene polymer may comprise substantially all the polymeric component. The polymeric component may further include other polymers or copolymers. The polymers may be selected to adjust the tackiness or viscosity as desired. The polymers may preferably be prevent in minor amounts. Preferably the butene polymer component comprises approximately 75% to 100% by weight of the polymeric component. The polymers may be selected from addition polymers e.g. rubbery polymers such as polyisobutylene vinyl polymers and acrylic polymers.

The polymeric component may include preferably a high molecular weight butene polymer component and a low molecular weight butene polymer. The components may be in the form of a blend. The high molecular weight butene polymer and low molecular weight butene polymer may be present in any suitable relative amounts which will allow for the creation of the desired degree of tackiness in order to repel various birds but with a high enough viscosity to minimize the flattening of the gel over an extended period. It will be understood that as the gel flattens the contamination thereof will increase and the efficiency of the composition as a repellant will accordingly decrease.

The at least one butene polymer may be a polybutene. The polybutene may be of the type sold under the trade designation HYVIS. These are synthetic hydrocarbon polymers manufactured by polymerization of olefins comprising isobutene. The polymers are long chain hydrophobic molecules with methyl group side chains. The polyisobutene sold under the designation HYVIS 10 and available from B.P. Trading Ltd. is particularly preferred as the low molecular weight component. HYVIS 10 has a molecular weight MW of approximately 900 - 1000. The polyisobuene polymer sold under the trade designation HYVIS 30 may be used as the high molecular weight component. HYVIS 30 has a molecular weight MW of approximately 1300–1500. The low molecular weight and high molecular weight isobutene polymers may be present in a weight ratio of approximately 1:1.

As an alternative as will be discussed below, the bird repellant composition may be manufactured utilizing the low molecular weight polymer only. If desired, the high molecular weight polymer component may be added at the end of the manufacturing process.

The thickening agent (b) of the bird repellant composition may be a hydrophobic thickening agent. The thickening agent may be an inorganic thickening agent. A clay based thickening agent may be used. An organophilic clay may be used. A thickening agent of the type sold under the trade designation TIXOGEL may be used. The TIXOGEL VP thickening agent available from United Catalysts Inc. is particularly preferred. The TIXOGEL is a clay based material containing montmorillionite and aluminium hydrosilicate together with suborganic radicals. The clay base material is solubilised in an organic medium.

The thickening agent may be present in a suitable amount which will provide the bird repellant composition with the requisite viscosity for use as a gel or bead composition. The thickening agent may be present in amounts of from 1-2 to 7% by weight, preferably 2.5 to 5% by weight, based on the weight of the total bird repellant composition. The thickening agent may be present in an amount of approximately 4 to 5% by weight based on the total amount of butene polymer.

The bird repellant composition according to the present invention may further include (c) a swelling agent.

The swelling agent may be a polar organic swelling agent. The swelling agent may be selected from alcohols and ketones. The swelling agent may be selected from methanol, acetone and methylethyl ketone and mixtures thereof. The swelling agent may be present in amounts of from 30 to 50% by weight based on the total weight of thickener and swelling agent. The swelling agent may be present in amounts of approximately 40% by weight based on the total amount of thickening agent in the bird repellant composition. The swelling agent may be present in amounts of from approximately 1 to 3%, preferably 2% by weight based on the weight of the total bird repellant composition.

A particularly preferred bird repellant composition according to the present invention includes a high molecular weight butene polymer and a low molecular weight butene polymer in approximately equal amounts. The total butene polymer content of the composition comprises 93% of the bird repellant composition. The other inert ingredients in the composition comprise the remaining 7% of the bird repellant composition. The bird repellant composition according to the present invention may further include other compounding ingredients. For example pesticides, fillers, extenders, colorants and other compounding ingredients may be included.

In accordance with a further aspect of the present invention there is provided a method of manufacturing a bird repellant composition of the type described above which includes (a) providing an effective amount of
  (i) a polymeric component which polymeric component includes at least one butene polymer or copolymer, and
  (ii) a thickening agent, and
(b) dispersing the thickening agent in the polymeric component.

The method of manufacturing a bird repellant composition according to this aspect of the present invention may further include the step of (c) swelling the dispersion so formed.

The dispersing of the thickening agent in the polymeric component may be conducted at elevated temperature. A temperature of approximately 45° to 55° C. may be used. The dispersing process may be continued as the temperature is raised from approximately 45° C. to approximately 55° C. The dispersion process may be conducted under high shear. The dispersion process may be conducted in a high speed mixer. The mixing process may continue for approximately 10 minutes.

The high speed mixing may then be continued for approximately 20 minutes or more as a swelling agent is added to the composition.

At the end of the period, the bird repellant composition may be filled into appropriate cartridges or left to stand as required. It will be understood that the ability to allow the composition to stand is a particular advantage in the art.

As discussed above the polymeric component may include a low molecular weight butene polymer component and a high molecular butene polymer weight component. Accordingly, the method of manufacturing a bird repellant composition may include as a preliminary step (a') blending a high molecular weight polybutene polymer and a low molecular weight polybutene polymer.

The blending of the two molecular weight polymers may be conducted at elevated temperatures as discussed above in relation to the dispersion step.

Alternatively, the method as described above may be run using the low molecular weight or high molecular weight polymer component alone. In this embodiment, the method of manufacturing a bird repellant composition may further comprise the step of (d) adding a further butene polymer component to the bird repellant composition so formed.

The addition of a further polybutene component at the end of the process may be conducted whilst the high shear (e.g. high speed mixing) is continued.

The present invention will now be more fully described in relation to the following examples. It should be understood, however, that the discussion following is illustrative only and should not be taken in any way as a restriction on the generality of the invention as described above.

EXAMPLE 1

Bird Repellant Composition

| Component | % by weight |
|---|---|
| Polybutene (MW 900–1000) | 46.5 |
| Polybutene (MW 1300–1500) | 46.5 |
| Thickening agent (TIXOGEN VP) | 5% |
| Swelling Agent (methylethyl ketone) | 2.0 |

Two grades of polybutene e.g. Hyvis 10 and Hyvis 30, were blended and heated in equal proportions into a suitable heated mixing vat. Blending continued until the temperature reached approximately 45°–55° C. The thickening agent (TIXOGEL VP) was mixed slowly into the polymer composition and mixing was continued for approximately 10 minutes.

The swelling agent (Methylethyl ketone) was then added and mixing continued for at least 20 minutes.

It has been found that the composition so formed may be provided in a cartridge form for delivery as a gel or bead. This has the particular advantage that it is possible to cover more area per tube than with a liquid or other coating formulation. The bird repellant composition in this form moreover, does not dry out as quickly as prior art products and minimizes flattening.

Further, the composition so formed is colourless and may be used in areas where a coloured gel would be a disadvantage.

EXAMPLE 2

Repellant Composition

| Component | % by weight |
|---|---|
| Polybutene (MW900–1000) | 46.5 |
| Polybutene (MW300–1500) | 46.5 |
| Thickening agent | 5.0 |
| Swelling agent | 2.0 |
| | 100.00 |

EXAMPLES OF ABOVE

Item 1. Hyvis 10
Item 2. Hyvis 30
Item 3. Tixogel VP
Item 4. Methanol, Acetone, MEK

METHOD OF MANUFACTURE 75 kgs of Polybutene (MW900-1000) is placed into suitable heated mixing vat, fitted with a high power agitator and heated to approximately 45°-55° C. While mixing slowly 8 kgs thickening agent is added and mixed till agent has been thoroughly dispersed. Then 3.2 kgs of swelling agent is slowly added and mixing continued for at least 20 minutes, after which time a considerable viscosity increase will be achieved.
is blended into composition and mixing continued till total mix is uniform. Mixer is turned off and product run into suitable containers or package as required.

Finally, it is to be understood that various other modifications and/or alterations may be made without departing from the spirit of the present invention as outlined herein.

We claim:

1. A bird repellant gel composition comprising:
   (a) about 75 to 98% by weight based on the total weight of the composition of a high molecular weight polybutene having a molecular weight of about 1300 to 1500 and a low molecular weight polybutene having a molecular weight of about 900 to 1000;
   (b) about 1 to 7% by weight based on the total weight of the composition of a clay-based thickening agent; and
   (c) about 1 to 3% by weight based on the total weight of the composition of a polar organic solvent swelling agent;
   said bird repellant composition having sufficient tackiness to repel birds and with sufficient viscosity to minimize the flattening of an applied bead of said composition.

2. The bird repellant composition of claim 1 wherein the viscosity of said composition is suitable for use in a cartridge form.

3. The bird repellant composition of claim 2 wherein the high molecular weight polybutene and the low molecular weight polybutene are present in an amount of from about 92 to 97% by weight of the total composition.

4. The bird repellant composition of claim 3 wherein the high molecular weight polybutene and the low molecular weight polybutene are present in a weight ratio of about 1:1.

5. The bird repellant composition of claim 1 wherein the swelling agent is selected from the group consisting of methanol, methyl ethyl ketone and mixtures thereof.

6. A method of preparing a bird repellant composition comprising:
   (a) blending a high molecular weight polybutene having a molecular weight of about 1300 to 1500 with a low molecular weight polybutene having a molecular weight of about 900 to 1000 at temperatures of about 45° to 55° C.;
   (b) dispersing about 1 to 7% by weight based on the total weight of the composition of a clay thickening agent to 75 to 98% by weight based on the total weight of the composition of the polybutene blend; and
   (c) swelling the dispersion so formed by adding thereto 1 to 3% by weight based on the total weight of the composition of a polar organic solvent swelling agent.

7. The method of claim 6 wherein the dispersion of step (b) is conducted at a temperature of approximately 45° to 55° C. under high shear for about 10 minutes.

8. The method of claim 7 wherein the polar organic solvent is added to the dispersion with high shear mixing for at least about 20 minutes.

9. A method of preparing a bird repellant composition comprising:
   (a) dispersing about 1 to 7% by weight based on the total weight of the composition of a clay thickening agent in a low molecular weight polybutene having a molecular weight of about 900 to 1000 at about 45° to 55° C.;
   (b) swelling the dispersion so formed by adding thereto 1 to 3% by weight of the total composition of a polar organic solvent swelling agent; and
   (c) adding a high molecular weight polybutene having a molecular weight of about 1300 to 1500 to the swollen dispersion at a temperature of about 45° to 55° C. with high shear mixing to form a substantially homogeneous blend, wherein the high molecular weight polybutene and the low molecular weight polybutene are about 75 to 98% by weight of the composition.

* * * * *

UNITED STATES PATENT AND TRADEMARK OFFICE
CERTIFICATE OF CORRECTION

PATENT NO. : 4,992,269
DATED : February 12, 1991
INVENTOR(S) : Snow et al.

It is certified that error appears in the above-identified patent and that said Letters Patent is hereby corrected as shown below:

At Col. 2, line 9, for "prevent" read --present--.

At Col. 2, line 38, for "polyisobuene" read --polyisobutene--.

At Col. 5, line 12, before "is blended" start a new paragraph and insert --An additional 75 kgs of Polybutene (MW 1300-1500)--.

Signed and Sealed this

Eighth Day of September, 1992

Attest:

DOUGLAS B. COMER

Attesting Officer  Acting Commissioner of Patents and Trademarks